US011648202B2

(12) United States Patent
Pauli et al.

(10) Patent No.: US 11,648,202 B2
(45) Date of Patent: May 16, 2023

(54) HYDROXYCHLOROQUINE SULFATE FORMULATIONS AND METHODS FOR PREPARATION AND USE THEREOF

(71) Applicant: Research Triangle Institute, Research Triangle Park, NC (US)

(72) Inventors: Elliott Richard Pauli, Chapel Hill, NC (US); Hemant N. Joshi, Parsippany, NJ (US); Anvit S. Vasavada, Harrison, NJ (US)

(73) Assignee: Research Triangle Institute, Research Triangle Park, NC (US)

( * ) Notice: Subject to any disclaimer, the term of this patent is extended or adjusted under 35 U.S.C. 154(b) by 124 days.

(21) Appl. No.: 16/650,965

(22) PCT Filed: Oct. 11, 2018

(86) PCT No.: PCT/US2018/055454
§ 371 (c)(1),
(2) Date: Mar. 26, 2020

(87) PCT Pub. No.: WO2019/075229
PCT Pub. Date: Apr. 18, 2019

(65) Prior Publication Data
US 2020/0297636 A1    Sep. 24, 2020

Related U.S. Application Data

(60) Provisional application No. 62/572,044, filed on Oct. 13, 2017.

(51) Int. Cl.
*A61K 9/16* (2006.01)
*A61K 9/48* (2006.01)
*A61K 31/4706* (2006.01)

(52) U.S. Cl.
CPC .......... *A61K 9/1652* (2013.01); *A61K 9/1658* (2013.01); *A61K 9/4816* (2013.01); *A61K 9/4866* (2013.01); *A61K 31/4706* (2013.01)

(58) Field of Classification Search
None
See application file for complete search history.

(56) References Cited

FOREIGN PATENT DOCUMENTS

CN    102349877 A       2/2012
CN    102525969 A  *    7/2012
(Continued)

OTHER PUBLICATIONS

Sharma et al. (Flavouring agents in pharmaceutical formulations, Ancient Sciences of Life, vol. VIII, No. 1, Jul. 1988, pp. 38-40). (Year: 1988).*

(Continued)

*Primary Examiner* — Melissa S Mercier
(74) *Attorney, Agent, or Firm* — NK Patent Law (57) ABSTRACT

Water-dispersible pharmaceutical compositions of hydroxychloroquine sulfate in powder or granule form are provided that allow for ease of preparation of measured-dose, liquid suspensions that are palatable and suitable for pediatric administration. The compositions in granular or powder form are efficiently dissolvable in water and can be provided encapsulated within a two-piece releasable hard capsule or a packet or pouch for easy release. An ion-pairing agent is present in the formulation of the composition that masks the bitter taste of the hydroxychloroquine sulfate, significantly reducing the need for addition of a sweetening agent. Methods are provided for preparing the water-dispersible pharmaceutical compositions of hydroxychloroquine sulfate and for preparing palatable weight-based pediatric doses.

19 Claims, 2 Drawing Sheets

(56) References Cited

FOREIGN PATENT DOCUMENTS

| | | | | | |
|---|---|---|---|---|---|
| CN | 102525969 | A | * | 7/2012 | |
| CN | 102525969 | B | * | 5/2015 | |
| CN | 102525969 | B | | 5/2015 | |
| EP | 2561868 | A1 | | 2/2013 | |
| WO | WO-2006079343 | A1 | * | 8/2006 | ............ A23G 4/043 |
| WO | 2008084504 | A2 | | 7/2008 | |
| WO | 2012068076 | A2 | | 5/2012 | |
| WO | WO-2012068076 | A2 | * | 5/2012 | ........... A61K 31/137 |

OTHER PUBLICATIONS

Biyani (Pharmaceutical Technology, Pharmaceutical Technology, Oct. 2, 2017, vol. 41, Issue 10, pp. 36-41). (Year: 2017).*

WIPO; International Preliminary Report on Patentability for International Patent Application No. PCT/US2018/055454 dated Apr. 23, 2020, 11 pages.

ISA/KR; International Search Report and Written Opinion for International Patent Application No. PCT/US18/55454 dated Feb. 11, 2019, 14 pages.

Al-Bari, AA. Feb. 17, 2015. Chloroquine analogues in drug discovery: new directions of uses, mechanisms of actions and toxic manifestations from malaria to multifarious diseases. J Antimicrob Chemother 70: 1608-1621.

Akhavan PS, Su J, Lou W, Gladman DD, Urowitz MB, and Fortin PR. 2013. The early protective effect of hydroxychloroquine on the risk of cumulative damage in patients with systemic lupus erythematosus. J of Rheumatol. 40: 6, 831-841.

Cao B, Parnell LA, Diamond MS, and Mysorekar IU. Jun. 12, 2017. Inhibition of autophagy limits vertical transmission of Zika virus in pregnant mice. J Exp M ed.

Center for Disease Control and Prevention (CDC). Dec. 11, 2019. Guidelines for Treating Malaria in the United States. Available from: https://www.cdc.gov/malaria/resources/pdf/treatmenttable.pdf.

Center for Disease Control and Prevention (CDC). Mar. 5, 2019. Rheumatoid arthritis. Available from: https://www.cdc.gov/arthritis/basics/rheumatoid-arthritis.html.

Center for Disease Control and Prevention (CDC). Medicines for the prevention of malaria while traveling. Hydroxychloroquine (Plaquenil™). Available from: https://www.cdc.gov/malaria/resources/pdf/fsp/drugs/hydroxychloroquine.pdf.

Helmick CG, Felson DT, Lawrence RC, Gabriel S, Hirsch R, Kwoh CK, Liang MH, Kremers HM, Mayes MD, Merkel PA, Pillemer SR, Reveille JD, Stone JH, for the National Arthritis Data Workgroup. Jan. 2008. Estimates of the Prevalence of Arthritis and Other Rheumatic Conditions in the United States. Part I.Arthritis Rheum. 58(1):15-25.

Kamphuis S and Silverman ED. Aug. 3, 2010. Prevalence and burden of pediatric-onset systemic lupus erythematosus. Nat Rev. Rheumatol. 6, 538-546.

Merrill JT [Article featured on the National Resource Center on Lupus Foundation website. Reviewed 2013. Why are treatments that were developed for malaria now widely used for lupus? Available from: http://www.resources.lupus.org/entry/malaria-drugs-used-on-lupus-patients.

Njaria PM, Okombo J, Njuguna NM, Chibale K. 2015. Chloroquine-containing compounds: a patent review (May 26, 2015). Expt Opin on Ther Patents. 25(9): 1003-1024.

Plaquenil® (hydroxychloroquine sulfate tablets, USP). FDA Approved Labeling for Plaquenil. Jan. 2017. St. Michael, Barbados, Concordia Pharmaceuticals Inc. Available from: https://www.accessdata.fda.gov/drugsatfda_docs/label/2017/009768s037s045s047lbl.pdf.

Ponticelli C, Moroni G. Mar. 2017. Hydroxychloroquine in systemic lupus erythematosus (SLE). Exp Opin Drug Safety. 16(3).

Ruiz-Irastorza G, Ramos-Casals M, Brito-Zeron P, Khamashta MA. Jan. 2010. Clinical efficacy and side effects of antimalarials in systemic lupus erythematosus: A systematic review. Ann Rheum Dis, 69: 20-28.

Sodium CMC information sheet. Prepared at the 28th JECFA (1984), published in FNP 31/2 (1984) and in FNP 52 (1992). Metals and arsenic specifications revised at the 55th JECFA (2000). An ADI 'not specified' was established for modified celluloses at the 35th JECFA (1989) http://www.fao.org/ag/agn/jecfa-additives/specs/Monograph I/additive-396-m1.pdf.

Thakral A, Klein-Gitelman MS. Dec. 2016. An update on treatment and management of pediatric systemic lupus erythematosus. Rheumatol Ther. 3(2):209-219.

The National Resource Center on Lupus. Oct. 6, 2016. Lupus facts and statistics. Available from: http://www.resources.lupus.org/entry/facts-and-statistics.

World Health Organization (WHO). Jan. 14, 2020. Malaria Fact Sheet. Geneva: WHO. Available from: http://www.who.int/mediacentre/factsheets/fs094/en/.

* cited by examiner

HYDROXYCHLOROQUINE SULFATE FORMULATIONS AND METHODS FOR PREPARATION AND USE THEREOF

CROSS-REFERENCE TO RELATED APPLICATIONS

This application is a U.S. National Stage application of International Patent Application No. PCT/US18/55454, filed Oct. 11, 2018, which claims the benefit of priority of U.S. provisional patent application No. 62/572,044 titled "HYDROXYCHLOROQUINE SULFATE FORMULATIONS AND METHODS FOR PREPARATION AND USE THEREOF," filed Oct. 13, 2017, each of which is incorporated by reference herein in its entirety.

TECHNICAL FIELD

The present disclosure relates to formulations of hydroxychloroquine sulfate that facilitate pediatric weight-base dosing.

BACKGROUND

Hydroxychloroquine sulfate (HCQS) is considered a generally safe drug that has anti-malarial properties and is used for treatment of lupus erythematosus and rheumatoid arthritis in adults, children, and even pregnant or nursing mothers. More recently, new indications for HCQS are being investigated and include cancer, dermatological issues, cardiovascular diseases, and prevention of transmission of Zika virus from mother to fetus during pregnancy (Al-Bari, 2015; Cao et al., 2017). Due to the low cost of production, tolerability, and discovery of unique biochemical properties of chloroquine-derived drugs, efforts to repurpose and reposition HCQS are being pursued (Njaria et al., 2015).

Malaria is an acute febrile illness that is caused by *Plasmodium* parasites which are spread through the bites of infected female *Anopheles* mosquitoes (WHO, Malaria Fact Sheet). While there are five *Plasmodium* species that cause malaria in humans, two of these species, *P. falciparum* and *P. vivax*, pose the greatest human threat (WHO, Malaria Fact Sheet). According to the latest World Health Organization (WHO) estimates, there were 212 million cases of malaria in 2015, which resulted in 429,000 deaths (WHO, Malaria Fact Sheet). Most of the malaria cases occurred in sub-Sahara Africa (90%), followed by South-East Asia (7%), and the Eastern Mediterranean (WHO, Malaria Fact Sheet). In 2015, 70% of the malaria-related deaths (303,000) were children under the age of 5 years (WHO, Malaria Fact Sheet). HCQS can be used for the prevention or treatment of uncomplicated malaria due to *P. malariae, P. ovale*, and susceptible strains of *P. falciparum* or *P. vivax*, in regions where chloroquine-containing drugs are still effective (CDC, Hydroxychloroquine [PLAQUENIL]). Central America west of the Panama Canal, Haiti, the Dominican Republic, and most of the Middle East are still responsive to chloroquine treatment and HCQS can be taken by adults, children, pregnant women, and nursing mothers traveling to those regions (CDC, Guidelines for Treating Malaria in the US). The WHO listed chloroquine-containing drugs in the Model List of Essential Medicines for Children in 2015 for treatment and prevention of *P. vivax* infection.

Dosing schemes of HCQS for prophylaxis therapy for malaria are typically as follows: Adults are prescribed 400 mg (310 mg base) of HCQS orally once per week at least one week before traveling to area where malaria transmission occurs. In addition, the same dose may be administered once per week while visiting the country, and four consecutive weeks after leaving. In the United States, pediatric doses may be on the same schedule as adults, but scaled to their body weight (CDC, Guidelines for Treating Malaria in the US). Pediatric populations may be prescribed, 6.5 mg/kg/dose (5 mg base/kg/dose; Max: 400 mg/dose or 310 mg base/dose) orally once every 7 days. Dosing may begin two weeks before entering an area where malaria transmission occurs and may continue for four weeks after leaving the endemic area.

Lupus is a chronic autoimmune disease where the body's immune system attacks and damages parts of the bodies such as skin, joints, and organs. The four types of lupus are: systemic lupus, cutaneous lupus, drug-induced lupus, and neonatal lupus. Systemic lupus erythematosus (SLE) accounts for approximately 70% of all cases, and often affects major organ or tissues in the body such as the heart, lungs, kidneys, or brain. Cutaneous (discoid) lupus affects only the skin and accounts for approximately 10% of the cases. Drug-induced lupus accounts for 10% of lupus cases and is similar to SLE, but is drug-induced and typically subsides when medications are discontinued. Neonatal lupus is a rare condition in which the mother's antibodies affect the fetus, with symptoms typically subsiding after 6 months of age. The Lupus Foundation of America estimates that 1.5 million Americans and at least 5 million people worldwide have a form of lupus. Lupus strikes mostly women of childbearing age and is two to three times more prevalent among women of color compared with Caucasian women. However, men, children, and teenagers can develop lupus (The National Resource Center of Lupus, Lupus facts and statistics). Pediatric onset of SLE represents 10 to 20% of all SLE cases and is associated with higher disease severity, including more-rapid damage accrual than adult-onset SLE (Kamphuis and Silverman, 2010).

For treatment of lupus, adults may be prescribed 200 to 400 mg (155 to 310 mg base) HCQS orally as a single dose or in two divided doses. Pediatric patients may be prescribed 4 to 6 mg HCQS/kg body weight/day with a maximum prescribed dose of 400 mg HCQS per day.

Rheumatoid arthritis (RA) is an inflammatory, autoimmune disease that mainly attacks the joints and joint tissue. An estimated 1.5 million Americans or about 0.6% of the United States population have rheumatoid arthritis (Helmick et al, 2008), and RA affects 2 to 3 times more women than men (CDC, Rheumatoid Arthritis). Juvenile idiopathic arthritis is a group of autoimmune, inflammatory disorders that affects approximately 294,000 children under the age of 16 years old and certain forms of this condition resemble adult rheumatoid arthritis. HCQS is indicated for the treatment of adult rheumatoid arthritis and works well for some for juvenile arthritis cases.

For treatment of rheumatoid arthritis, adults may be prescribed 200 to 400 mg (155 to 310 mg base) HCQS orally as a single dose or in two divided doses.

Currently, in the United States HCQS is sold as the brand name PLAQUENIL or as a generic medicine that is only available in tablets of 155 mg base or 200 mg salt. Thus, for pediatric dosing, a pharmacist must strip the outer film-coating, crush the tablets, and then suspend the powder in water with a flavoring agent like ORA-PLUS. This stripping and crushing process is cumbersome, the suspension media such as ORA-PLUS is costly, and the process results in a loss of active pharmaceutical ingredient.

Thus, there is an unmet need for improved HCQS formulations that are amenable for dosing children. The present invention provides such improved compositions, and methods of preparation and use thereof.

SUMMARY

In one embodiment, a water-dispersible pharmaceutical composition is provided comprising:
- (a) about 5 wt. % to about 30 wt. % hydroxychloroquine sulfate;
- (b) about 5 wt. % to about 80 wt. % of an ion-pairing agent;
- (c) optionally, about 0.1 wt. % to about 20 wt. %, on a dry weight basis, of an alkalinizing agent;
- (d) about 1 wt % to about 60 wt % of a diluent;
- (e) optionally about 0.1 wt. % to about 20 wt. % of one or more of sweetening agents, coloring agents and flavoring agents;
- (I) optionally about 1 wt. % to about 80 wt. % of a disintegrating agent or a disintegrant; and
- (g) optionally up to about 20 wt. % of one or more of an additional excipients and adjuvants, wherein the sum of (a)-(g) is 100%, and wherein the pharmaceutical composition is in the form of a granule or a powder.

In one embodiment, a water-dispersible pharmaceutical composition is provided comprising:
- (a) about 5 wt. % to about 30 wt. % hydroxychloroquine sulfate;
- (b) about 5 wt. % to about 80 wt. % of an ion-pairing agent;
- (c) optionally, about 0.1 wt. % to 20 wt. %, on a dry weight basis, of an alkalinizing agent;
- (d) about 0.1 wt. % to 20 wt. % of one or more of sweetening agents, coloring agents and flavoring agents; and
- (e) optionally about 0.1 wt. % to 20 wt. % of one or more of an additional excipients and adjuvants, wherein the sum of (a)-(e) is 100%, and wherein the pharmaceutical composition is in the form of a granule or a powder. The compositions mask the bitter taste of the hydroxychloroquine sulfate such that addition of a sweetening agent is significantly minimized and allow for efficient dissolution of the granule or powder in water. In one embodiment, the water-dispersible pharmaceutical compositions comprising hydroxychloroquine sulfate are encapsulated within a two-piece releasable hard capsule or a packet or pouch. The encapsulated forms of the pharmaceutical composition allow for ease of preparation of pediatric weight-based doses.

In one embodiment, a process is provided for preparing the water-dispersible pharmaceutical compositions comprising hydroxychloroquine sulfate, comprising: combining a hydroxychloroquine sulfate, an ion-pairing agent, and optionally one or more excipients and adjuvants; granulating the combination with water or with an alkalinizing agent in water; drying the granules; and optionally, combining the dried granules with one or more of sweetening agents, coloring agents, flavoring agents, excipients, and adjuvants.

In one embodiment, a method is provided for preparing measured-dose liquid suspension of a hydroxychloroquine sulfate pharmaceutical composition, the method comprising: releasing a water-dispersible pharmaceutical composition comprising hydroxychloroquine sulfate in granule or powder form that is encapsulated within a two-piece releasable hard capsule or a packet or a pouch; and dissolving or suspending a measured-dose of the released granule or powder in water.

DETAILED DESCRIPTION

Chloroquine is one of the bitterest compounds. The bitterness index of caffeine is 46, which is a known bitter compound. Bitterness indices of chloroquine sulfate and chloroquine are 249 and 87, respectively. Thus, it is not easy to mask the bitterness of chloroquine sulfate.

The present invention features water-dispersible pharmaceutical compositions comprising the active ingredient hydroxychloroquine sulfate (HCQS) Formula (I) in granule or powder form that allow for efficient preparation of measured-dose, palatable liquid suspensions suitable for pediatric dosing.

Formula (I) or Compound (I)

Surprisingly it has been found that the ease of dispersing hydroxychloroquine (HCQS) in an aqueous medium and masking its bitter taste can be dramatically increased by formulating the HCQS with an ion-pairing agent and an alkalinizing agent that increases the pH to between about pH 7 to 8. In one aspect of the present invention, a pharmaceutical composition is provided comprising: (a) about 5 wt. % to about 30 wt. % HCQS sulfate; (b) about 5 wt. % to about 80 wt. % of an ion-pairing agent; (c) optionally, about 0.1 wt. % to about 20 wt. %, on a dry weight basis, of an alkalinizing agent; (d) about 0.1 wt. % to about 20 wt. % of one or more of sweetening agents, coloring agents and flavoring agents; and (e) of one or more of an additional excipients and adjuvants, wherein the sum of (a)-(e) is 100%, and wherein the pharmaceutical composition is in the form of a granule or a powder. The formulation reduces the bitter taste of the HCQS such that an addition of a sweetening agent is minimized or unnecessary and allows for efficient dissolution of the granule or powder in water.

Throughout this specification and the claims, the terms "comprise," "comprises," and "comprising" are used in a non-exclusive sense, except where the context requires otherwise. Likewise, the terms "having" and "including" and their grammatical variants are intended to be non-limiting, such that recitation of items in a list is not to the exclusion of other like items that can be substituted or added to the listed items.

Throughout this specification and the claims, the terms "dissolution", "dispersion", and "suspension" and their grammatical variants are used interchangeably and are intended to mean that a composition is capable of being suspended or dispersed in an aqueous solution and may also be capable of being partially or completely solubilized or dissolved in the aqueous solution.

HCQS is available in the United States market in a 200 mg (155 mg base) tablet formulation (REFERENCE LISTED DRUG—PLAQUENIL from Concordia Pharma). PLAQUENIL and generic tablets are all an immediate release tablet formulations. Currently, pediatric formulations of hydroxychloroquine are not available even though HCQS is a widely used antimalarial drug. Thus, for dosing by weight for children, prior art HCQS tablets have to be stripped of their coating, crushed, and suspended in water with a flavoring agent like ORA-PLUS. This stripping and crushing process is cumbersome, the suspension media such as ORA-PLUS is costly, and the process results in a loss of active pharmaceutical ingredient. In addition, the shelf-life of such a suspension tends to be only 30 days at 2-8° C. protected from light. In many instances, the suspension media ORA-PLUS may not be easily available.

The present invention solves these problems with granular and powder formulations of HCQS that can be provided encapsulated in capsules, packets or pouches as well as in tablet form such that the encapsulated formulations can be released very easily and added to an aqueous medium in a measured dose in order to easily prepare a palatable liquid suspension. The suspended formulations can be administered to children while the unaltered original capsules are also useful for administration to adults. The suspended formulation masks the bitter taste of the hydroxychloroquine sulfate and allows for efficient dispersion and dissolution of the granules or powder in water.

Another advantage of the present invention is that the pharmaceutical compositions in the granular and powder form are stable at room temperature for 2 years.

The powder and granule pharmaceutical compositions of the present invention dissolve or suspend when added to water. Thus, the compositions provide improved solubilization over the poorly water-soluble prior art HCQS tablets. The pharmaceutical compositions according to the present invention provide for immediate release of the HCQS.

Example 1 herein describes preparation of a water-dispersible HCQS granule pharmaceutical composition. In one aspect of the present invention, water-dispersible pharmaceutical compositions are provided comprising:
  (a) about 5 wt. % to about 30 wt. % hydroxychloroquine sulfate;
  (b) about 5 wt. % to about 80 wt. % of an ion-pairing agent;
  (c) optionally, about 0.1 wt. % to about 20 wt. %, on a dry weight basis, of an alkalinizing agent;
  (d) about 1 wt. % to about 60 wt. % of a diluent;
  (e) optionally about 0.1 wt. % to about 20 wt. % of one or more of sweetening agents, coloring agents and flavoring agents;
  (f) optionally about 1 wt. % to about 80 wt. % of a disintegrating agent or a disintegrant; and
  (g) optionally up to about 20 wt. % of one or more of an additional excipients and adjuvants,
wherein the sum of (a)-(g) is 100%, and wherein the pharmaceutical composition is in the form of a granule or a powder.

Suitable ion pairing agents include, but are not limited to, one or a combination of sodium carboxymethyl cellulose (NaCMC), sodium alginate, acrylic acid polymer, methacrylate polymers (Eudragits), deoxycholic acid, sodium EDTA, sodium citrate, sodium fumarate, fumaric acid, sodium glutamate, potassium sorbate, calcium sulfate, sodium phosphate, potassium phosphate, and glutamic acid. The ion pairing agent can be NaCMC. The average molecular weight of the CMC can be about 10,000 to 200,000. The ion pairing agent can be sodium citrate.

The pharmaceutical compositions can be in the form of a tablet or a hard-shell capsule. The pharmaceutical compositions can be provided in a dosage unit of 20 mg to 200 mg of HCQS. The dosage unit can be 200 mg of HCQS as currently sold in the United States.

The pharmaceutical compositions in the powder or granular form can be stable at room temperature for 2 years.

It is one objective of the present invention to provide pharmaceutical compositions comprising HCQS that can be prepared efficiently in measured-dose liquid suspensions that are palatable for oral administration. Thus, in one feature of the present invention, the water-dispersible pharmaceutical compositions comprising HCQS are provided encapsulated within a two-piece releasable hard capsule. Suitable capsules are known in the art and including capsules that consist essentially of hydroxypropyl methylcellulose and capsules that consist essentially of gelatin.

In one feature of the present invention, a method is provided that includes releasing the water-dispersible pharmaceutical composition encapsulated within a two-piece releasable hard capsule and dissolving or suspending a measured dose of the released granule or powder in an aqueous medium such as water.

In one feature of the present invention, a method is provided that includes releasing the water-dispersible pharmaceutical composition encapsulated within a packet or a pouch and dissolving or suspending a measured dose of the released granule or powder in an aqueous medium such as water.

In one feature of the present invention, the released granule or powder can be dissolved in alkaline water.

A preferred pH of the liquid suspension ranges from about pH 7 to 8. Accordingly, the formulation is preferably suspended in water, and the acidic media (including, for example, soda and orange juice) are to be avoided. An alkanizing agent can be included in the pharmaceutical composition to achieve the preferred pH range of the liquid suspension of about 7-8.

Suitable alkanizing agents include, but are not limited to, one or a combination of sodium hydroxide, potassium hydroxide, sodium bicarbonate, potassium bicarbonate, sodium carbonate, potassium carbonate, calcium phosphate, dibasic sodium phosphate, dibasic potassium phosphate, and meglumine. The alkanizing agent can be sodium hydroxide.

A sweetening agent and/or a flavoring agent can be included in the pharmaceutical compositions of the present invention to further increase the palatability of the liquid suspensions. The sweetening agents are preferably non-acidic sweetening agents. Suitable sweetening agents include, but are not limited to, one or a combination of fructose, glucose, sucrose, erythritol, sorbitol, mannitol, xylitol, honey, maple syrup, sucralose, saccharin, aspartame, neotame, and advantame.

A disintegrating agent or a disintegrant can be included in the water-dispersible pharmaceutical compositions of the present invention to aid dissolution in the aqueous medium. The disintegrating agent includes, but is not limited to, one or a combination of sodium starch glycolate, crospovidone, and croscarmellose sodium. The disintegration agent can be sodium starch glycolate.

Regarding the diluents that can be included in the water-dispersible pharmaceutical compositions of the present invention, suitable diluents include, but are not limited to, one or a combination of glycerine, starches, hydrolyzed starches, partially pregelatinized starches, anhydrous lactose, lactose monohydrate, sugar alcohols, sorbitol, xylitol, and mannitol.

Additional excipients and adjuvants can be included in the pharmaceutical compositions of the present invention, and are selected from binders, carriers, lubricants, flow control agents, and crystallization retarders.

In another aspect of the present invention, a pharmaceutical composition is provided comprising: (a) about 5 wt. % to about 30 wt. % HCQS sulfate; (b) about 5 wt. % to about 80 wt. % of an ion-pairing agent; (c) optionally, about 0.1 wt. % to about 20 wt. %, on a dry weight basis, of an alkalinizing agent; (d) about 0.1 wt. % to about 20 wt. % of one or more of sweetening agents, coloring agents and flavoring agents; and (e) of one or more of an additional excipients and adjuvants, wherein the sum of (a)-(e) is 100%, and wherein the pharmaceutical composition is in the form of a granule or a powder. The one or more of additional excipients and adjuvants can include, but is not limited to, sodium starch glycolate, crospovidone, croscarmellose sodium, glycerine, starches, hydrolyzed starches, partially pregelatinized starches, anhydrous lactose, lactose monohydrate, sugar alcohols, binders, carriers, lubricants, flow control agents, or crystallization retarders.

In one feature of the present invention, a process is provided for preparing the water-dispersible pharmaceutical compositions in powder or granular form. The process includes combining HCQS, an ion-pairing agent, and optionally one or more excipients and adjuvants; granulating the combination with water or with an alkalinizing agent in water, drying the granules; and optionally, combining the dried granules with one or more of sweetening agents, coloring agents, flavoring agents, excipients, and adjuvants.

Example 2 describes bitterness analysis of liquid suspensions of the compositions using an electronic tongue. Liquid samples were prepared as shown in Table 1 below.

TABLE 1

Hydroxychloroquine sulfate sample set.

| # | Label | Product | Concentration | Code |
|---|-------|---------|---------------|------|
| 1 | Sample 1 | HCQS | 4 mg/mL at pH 7 | F1 |
| 2 | Sample 2 | HCQS with NaCMC | 4 mg/mL at pH 7 | F2 |
| 3 | Sample 3 | HCQS | 4 mg/mL at pH 8 | F3 |
| 4 | Sample 4 | HCQS with NaCMC | 4 mg/mL at pH 8 | F4 |
| 5 | Sample 5 | HCQS with NaCMC | 6.5 mg/mL at pH 8 | F5 |
| 6 | Sample 6 | HCQS with Na Citrate | 6.5 mg/mL at pH 8 | F6 |

Figure 1:
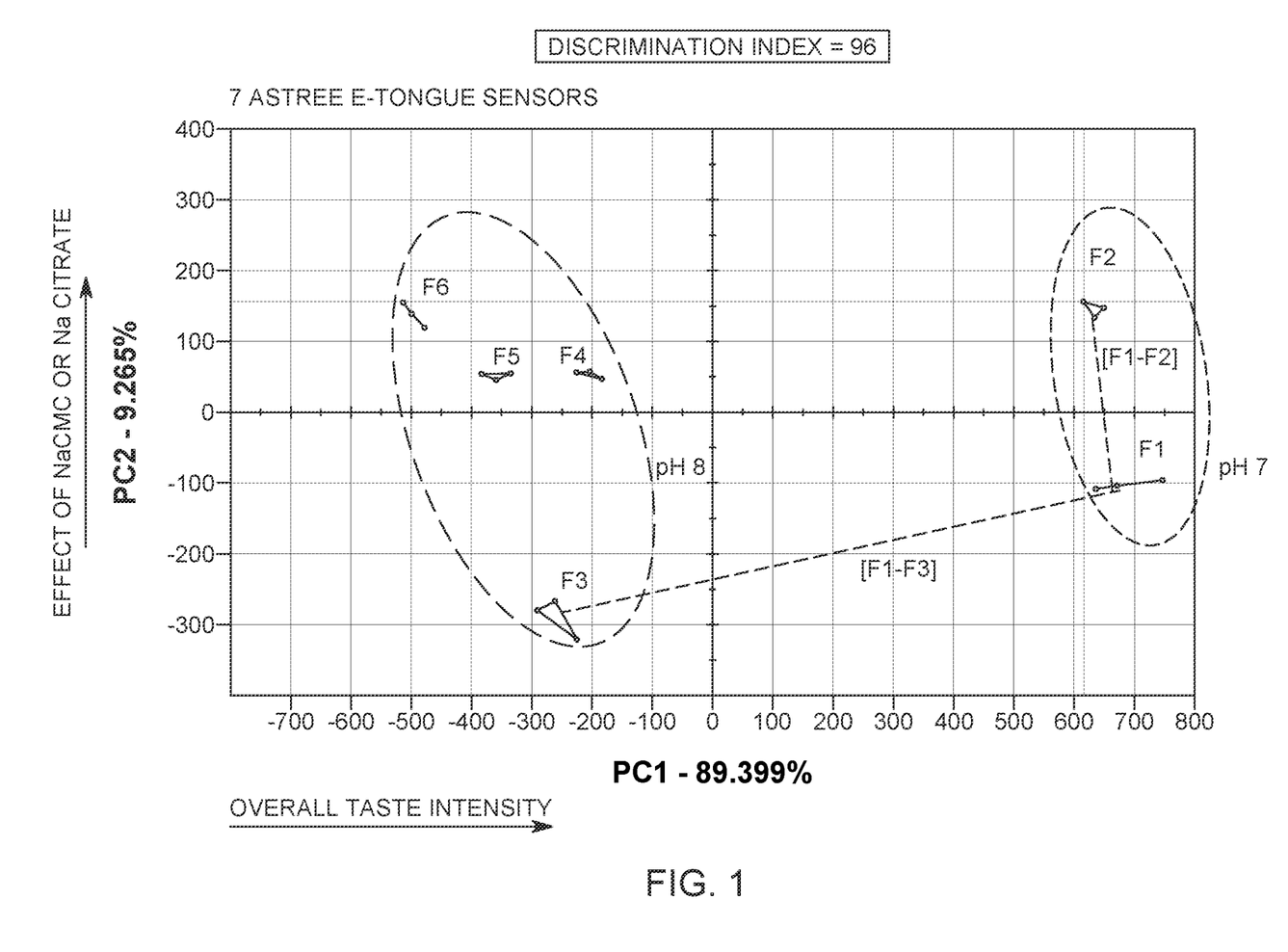
FIG. 1 is a taste map based on the principal component analysis (PCA) of HCQS formulations.
Figure 2:
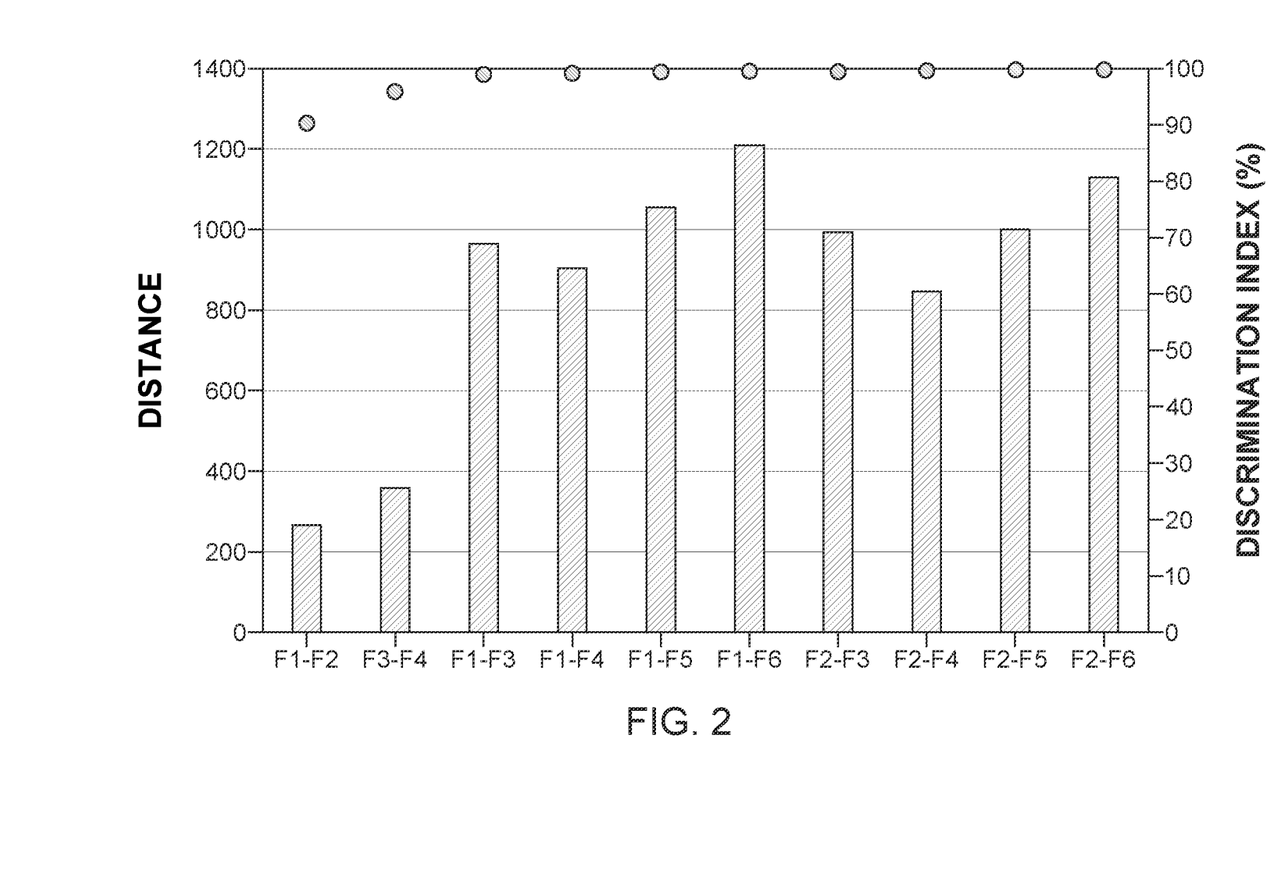
FIG. 2 is a line chart showing the distance between HCQS formulations.

A taste map based on Principal Component Analysis (PCA) is shown in FIG. 1. There is a significant difference between the taste of the HCQS sample prepared at pH 7 (F1, F2) and the samples prepared at pH 8 (F3, F4, F5, F6). Samples prepared at pH 8 without or with NACMC or Na citrate are less bitter than the HCQS prepared in water at pH 7. Euclidian distances between the HCQS formulations to assess taste proximity between samples are shown in FIG. 2. The distance (264) value of pair [F1-F2] shows that the ion-pairing agent NaCMC impacts the taste of the HCQS at pH 7. The same is shown for pair [F3-F4] prepared at pH 8. The distance (965) value for pair [F1-F3] shows that the increase from pH 7 to 8 significantly modified the taste of the preparation. Thus, the HQSC pharmaceutical compositions of the present invention have Euclidian distances of at least about 260 or greater relative to a control composition, wherein the Euclidian distance is calculated with an e-tongue system for an aqueous suspension of 0.1-25 mg/ml of the composition at a pH ranging from about 7 to about 8, wherein the composition and the control composition are the same other than the absence of the ion-pairing agent from the control composition.

EXAMPLES

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter.

Example 1

Preparation of a Water Dispersible Hydroxychloroquine Sulfate Formulation

A water-dispersible, granular formulation of hydroxychloroquine sulfate was developed as described. An addition of 200 milligram HCQS to 50 mL water (4 mg HCQSS/mL), results in an extremely bitter tasting solution. The following approaches were undertaken in an attempt to mask the bitter taste of the HCQS:

1. 5% Corn starch solution was prepared and added to a mixture of HCQS and lactose monohydrate. The granules were dried at 40° C.

2. 1% Na-CMC solution was prepared and added to the mixture of HCQS and lactose monohydrate. The granules were dried at 40° C.

3. 5% Corn starch solution and Eudragit L100 polymer was mixed with HCQS and dried at 40° C.

4. 5% Na-CMC solution was mixed with HCQS and Lactose monohydrate and dried at 40° C.

5. 3% Na-CMC solution (+1 gm Glycerine) and Eudragit L100 polymer was mixed with HCQS and granulated.

6. HCQS was granulated with 3% Na-CMC+Glycerine, dried at 40° C. Sorbitol powder and Aspartame was added and the mixture was again granulated.

7. HCQS was granulated with 3% Na-CMC+Glycerine, dried at 40° C. and passed through 20 mesh sieve. Sorbitol powder and Aspartame were added and the mixture was again granulated with 3% Na-CMC+Glycerine, dried at 40° C. and passed through 20 mesh sieve. About 480 mg of granules which contained 200 mg of HCQS were added to 100 mL water, which resulted in a minimal bitter taste. Additional (100 mg) sodium CMC was added to the solution along with about 5 mg of aspartame. The bitter taste was tolerable, but the sweetness needed to be increased further.

In another approach, the granules of drug with CMC were coated with GELEOL, PRECIROL or COMPRITOL (Gattefosse, N.J.). These components were softened at about 50-60° C. and the granules were mixed. These components dissolve in water over time and can help to mask the bitter taste. Additional sodium CMC may be added to the granules to further mask the bitter taste.

In the course of the experiments, 25 mg to 300 mg of sodium CMC was added to 200 mg HCQS. As the amount of sodium CMC was increased, the bitterness decreased. It is believed that the sodium CMC forms an ion pair with the HCQS, which in turn masks the bitter taste.

The pKa of the amine of HCQS is about 9.4. Thus, at pH values less than the pKa value, the HCQS will be in the ionized form and will dissolve in aqueous solution. Thus, an ideal pH of the HCQS suspension is about 7 to 8 at which it will ion-pair with the sodium CMC and bitterness will be reduced. To achieve this pH range, 1 N NaOH was included in the granulation step which imparted sufficient alkalinity to the granules to allow for pH 7-8 when the mixture was dissolved in water. Accordingly, the formulation is desirably suspended in water, and acidic media (including, for example, soda and orange juice) are to be avoided.

Example 2

Electronic Tongue Bitterness Analysis of Hydroxychloroquine Sulfate Liquid Suspensions The objective of this experiment was to quantitatively compare the bitterness of hydroxychloroquine sulfate (HCQS) in the presence of two ion pairing agents, NaCMC and Na-citrate, at either pH 7 or 8 in liquid suspensions suitable for oral administration.

An Astree electronic tongue was used to compare the effectiveness of the HCQS taste masking in the liquid formulations. The bitterness masking effect of each formulation was estimated by determination of the distances between e-tongue signal of a formulation containing the HCQS and the formulation without HCQS (placebo). The best masking formulation is the one giving the optimum distance. The HCQS tested are shown in Table 1.

TABLE 1

Hydroxychloroquine sulfate sample set.

| # | Label | Product | Concentration | Code |
|---|-------|---------|---------------|------|
| 1 | Sample 1 | HCQS | 4 mg/mL at pH 7 | F1 |
| 2 | Sample 2 | HCQS with NaCMC | 4 mg/mL at pH 7 | F2 |
| 3 | Sample 3 | HCQS | 4 mg/mL at pH 8 | F3 |
| 4 | Sample 4 | HCQS with NaCMC | 4 mg/mL at pH 8 | F4 |
| 5 | Sample 5 | HCQS with NaCMC | 6.5 mg/mL at pH 8 | F5 |
| 6 | Sample 6 | HCQS with Na Citrate | 6.5 mg/mL at pH 8 | F6 |

The assays were performed on an Astree e-tongue system equipped with an Alpha M.O.S. sensor set for pharmaceutical analysis composed of 7 specific sensors. The 48-position auto-sampler and 25 ml-beakers were used for sampling. Acquisition times were fixed at 120s. All the data generated on Astree system were treated using multidimensional statistics on AlphaSoft V14.3 software.

The sample suspensions were poured directly in the beakers for analysis by the Astree e-tongue. The analytical conditions for the experiment were as follows:
Sample volume: 25 ml
Acquisition time: 120 s
Time per analysis: 180 s
The e-tongue signal in each solution was measured at the equilibrium on 7 sensors (average between 100 and 120 s). Three replicates were used for the analysis.
Astree sensors were cleaned up 4 times in deionized water between each measurement to avoid cross-contamination.

The signal of each sensor on each assay was integrated in a matrix of data that was computed by multidimensional statistic tools. A taste map based on Principal Component Analysis (PCA) was generated using all sensors. The active ingredient is clearly discriminated along PC1 axis. There is a clear difference between the taste of HCQS prepared at pH 7 (F1, F2) and the samples prepared at pH 8 (F3, F4, F5, F6). Addition of the ion pairing agents NaCMC or Na-citrate impacted the taste of the formulations as well. Samples prepared at pH 8 without or with NACMC or Na citrate are less bitter than the HCQS prepared in water at pH 7.

The Euclidian distances between the HCQS formulations were calculated to assess taste proximity between samples: the lower the distance, the closer the taste. Also, a Discrimination Index (DI in %) was determined for each pair. This indicator takes into account the average difference between the pairs, as well as the dispersion of each sample. The closer the index values are to 100%, the greater the distance between the centers of gravity and the smaller the dispersion within the groups. Thus, the DI is useful to assess the significance of the difference between the groups.

The distance (264) and DI (90%) of pair [F1-F2] shows that the NaCMC impacts the taste of the HCQS at pH 7. The same observation was observed for pair [F3-F4] prepared at pH 8. The distance (965) and DI (99%) values for pair [F1-F3] show that the increase from pH 7 to 8 significantly modified the taste of the preparation. Overall, both variation of pH from 7 to 8 and addition of NaCMC or Na-citrate significantly affected the taste perception of the samples (DI=90-99%).

The repeatability of the measurements on Astree e-tongue was determined for each sample on 3 replicates (Table 2). The results show that the repeatability of the analysis is very good.

TABLE 2

Mean standard deviation (SD) and relative standard deviation (RSD) for each sample.

| Sample Name | SD | % RSD |
|-------------|------|-------|
| F1 | 13.5 | 0.5 |
| F2 | 9.7 | 0.4 |
| F3 | 12.9 | 0.5 |
| F4 | 7.5 | 0.3 |
| F5 | 8.0 | 0.3 |
| F6 | 8.1 | 0.3 |

In summary, the HCQS liquid formulations at pH 7 (F1, F2) taste significantly more bitter than the formulations at pH 8 (F3, F4, F5, F6). Addition of the ion pairing agent, NaCMC or Na citrate, to the formulations also significantly decreased the bitter taste. The HCQS liquid formulations at pH 8 that included either NaCMC or Na citrate were the least bitter.

Any patents or publications mentioned in this specification are indicative of the levels of those skilled in the art to which the present disclosure pertains. These patents and publications are herein incorporated by reference in their entirety to the same extent as if each individual publication was specifically and individually indicated to be incorporated by reference.

One skilled in the art will readily appreciate that the present disclosure is well adapted to carry out the objects and obtain the ends and advantages mentioned, as well as those inherent therein. The present Examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

REFERENCES

1. Al-Bari, A A. 2015. Chloroquine analogues in drug discovery: new directions of uses, mechanisms of actions and toxic manifestations from malaria to multifarious diseases. *J Antimicrob Chemother* 70:1608-1621.
2. Akhavan P S, Su J, Lou W, Gladman D D, Urowitz M B, and Fortin P R. 2013. The early protective effect of hydroxychloroquine on the risk of cumulative damage in patients with systemic lupus erythematosus. *J of Rheumatol.* 40: 6, 831-841.
3. Cao B, Parnell L A, Diamond M S, and Mysorekar I U. 2017. Inhibition of autophagy limits vertical transmission of Zika virus in pregnant mice. *J Exp Med* [Epub ahead of print].
4. Center for Disease Control and Prevention (CDC). 2013. Guidelines for Treating Malaria in the United States. Available from: https://www.cdc.gov/malaria/resources/pdf/treatmenttable.pdf.
5. Center for Disease Control and Prevention (CDC). 2017. Rheumatoid arthritis. Available from: https://www.cdc.gov/arthritis/basics/rheumatoid-arthritis.html.
6. Center for Disease Control and Prevention (CDC). Medicines for the prevention of malaria while traveling. Hydroxychloroquine (Plaquenil™) Available from: https://www.cdc.gov/malaria/resources/pdf/fsp/drugs/hydroxychloroquine.pdf
7. Helmick C G, Felson D T, Lawrence R C, Gabriel S, Hirsch R, Kwoh C K, Liang M H, Kremers H M, Mayes M D, Merkel P A, Pillemer S R, Reveille J D, Stone J H, for the National Arthritis Data Workgroup. 2008. Estimates of the Prevalence of Arthritis and Other Rheumatic Conditions in the United States. Part I. *Arthritis Rheum.* 58(1):15-25.
8. Kamphuis S and Silverman E D. 2010. Prevalence and burden of pediatric-onset systemic lupus erythematosus. *Nat Rev. Rheumatol.* 6, 538-546.
9. Merrill J T [Article featured on the National Resource Center on Lupus Foundation website. Reviewed 2013. Why are treatments that were developed for malaria now widely used for lupus? Available from: http://www.resources.lupus.org/entry/malaria-drugs-used-on-lupus-patients.
10. Njaria P M, Okombo J, Njuguna N M, Chibale K. 2015. Chloroquine-containing compounds: a patent review (2010 to 2014). *Expt Opin on Ther Patents.* 25(9): 1003-1024.
11. Plaquenil® (hydroxychloroquine sulfate tablets, USP). FDA Approved Labeling for Plaquenil. 2015. St. Michael, Barbados, Concordia Pharmaceuticals Inc. Available from: https://www.accessdata.fda.gov/drugsatfda_docs/label/2017/009768s037s045s 0471b1.pdf.
12. Ponticelli C, Moroni G. 2017. Hydroxychloroquine in systemic lupus erythematosus (SLE). *Exp Opin Drug Safety.* 16(3).
13. Ruiz-Irastorza G, Ramos-Casals M, Brito-Zeron P, Khamashta M A. 2010. Clinical efficacy and side effects of antimalarials in systemic lupus erythematosus: A systematic review. Ann Rheum Dis, 69: 20-28.
14. Sodium CMC information sheet. Prepared at the 28th JECFA (1984), published in FNP 31/2 (1984) and in FNP 52 (1992). Metals and arsenic specifications revised at the 55th JECFA (2000). An ADI 'not specified' was established for modified celluloses at the 35th JECFA (1989) http://www.fao.org/ag/agn/jecfa-additives/specs/Monographl/additive-396-m1.pdf.
15. Thakral A, Klein-Gitelman M S. 2016. An update on treatment and management of pediatric systemic lupus erythematosus. *Rheumatol Ther.* 3(2):209-219.
16. The National Resource Center on Lupus. 2017. Lupus facts and statistics. Available from: http://www.resources.lupus.org/entry/facts-and-statistics.
17. World Health Organization (WHO). 2017. Malaria Fact Sheet. Geneva: WHO. Available from: http://www.who.int/mediacentreffactsheets/fs094/en/.

That which is claimed:

1. A water-dispersible pharmaceutical composition for use in preparing a measured-dose liquid suspension, the composition comprising:
　(a) about 5 wt. % to about 30 wt. % hydroxychloroquine sulfate;
　(b) about 5 wt. % to about 80 wt. % of an ion-pairing agent, wherein the ion pairing agent comprises one or a combination of sodium carboxymethyl cellulose (CMC), alginic acid, sodium alginate, acrylic acid polymer, methacrylate polymers (Eudragits), deoxycholic acid, sodium deoxycholate, sodium EDTA, fumaric acid, sodium fumarate, sodium glutamate, sodium phosphate, and glutamic acid;
　(c) about 0.1 wt. % to about 20 wt. %, on a dry weight basis, of an alkalinizing agent;
　(d) about 1 wt % to about 60 wt % of a diluent;
　(e) optionally about 0.1 wt. % to about 20 wt. % of one or more of sweetening agents, coloring agents and flavoring agents;
　(f) optionally about 1 wt. % to about 80 wt. % of a disintegrating agent; and
　(g) optionally about 1 wt. % to 20 wt. % of one or more of an additional excipients and adjuvants,
　wherein the sum of (a)-(g) is 100%, wherein the pharmaceutical composition is in the form of a granule or a powder, and wherein the amount of alkalinizing agent present in the composition is selected to result in a pH of 8 for the measured-dose liquid suspension.

2. The pharmaceutical composition of claim 1, wherein the ion pairing agent is CMC.

3. The pharmaceutical composition of claim 2, wherein the CMC has an average molecular weight of about 10,000 to 200,000.

4. The pharmaceutical composition of claim 1, wherein the disintegrating agent comprises one or a combination of sodium starch glycolate, crospovidone, or croscarmellose sodium.

5. The pharmaceutical composition of claim 1, wherein the sweetening agent comprises one or a combination of fructose, glucose, sucrose, erythritol, sorbitol, mannitol, xylitol, honey, maple syrup, sucralose, saccharin, aspartame, neotame, or advantame.

6. The pharmaceutical composition of claim 1, wherein the alkanizing agent comprises one or more of potassium hydroxide, sodium bicarbonate, potassium bicarbonate, sodium carbonate, potassium carbonate, disodium phosphate, trisodium phosphate, dibasic potassium phosphate, or meglumine.

7. The pharmaceutical composition of claim 1, wherein the diluent comprises one or more of glycerine, starches, hydrolyzed starches, partially pregelatinized starches, anhydrous lactose, lactose monohydrate, sugar alcohols, sorbitol, xylitol, or mannitol.

8. The pharmaceutical composition of claim 1, wherein the additional excipients and adjuvants are selected from binders, carriers, lubricants, flow control agents, and crystallization retarders.

9. The pharmaceutical composition of claim 1, comprising a dosage unit of 20 mg to 200 mg of hydroxychloroquine sulfate.

10. The pharmaceutical composition of claim 1, comprising a dosage unit of 200 mg of hydroxychloroquine sulfate.

11. The pharmaceutical composition of claim 1, in the form of a tablet or a hard-shell capsule.

12. A water-dispersible pharmaceutical composition comprising hydroxychloroquine sulfate according to claim 1 encapsulated within a two-piece releasable hard capsule shell.

13. The pharmaceutical capsule of claim 12, wherein the capsule shell consists essentially of hydroxypropyl methylcellulose.

14. The pharmaceutical capsule of claim 12, wherein the capsule consists essentially of gelatin.

15. A process for preparing a pharmaceutical composition of claim 1, comprising:
    combining a hydroxychloroquine sulfate, an ion-pairing agent, and one or more excipients and adjuvants;
    granulating the combination with water or with an alkalinizing agent in water;
    drying the granules; and
    optionally, combining the dried granules with one or more of sweetening agents, coloring agents, flavoring agents, excipients, and adjuvants.

16. A method for preparing a measured-dose liquid suspension of the hydroxychloroquine sulfate pharmaceutical composition of claim 1, the method comprising: releasing the water-dispersible pharmaceutical composition according to claim 1 in a measured dose amount in water and dissolving the measured dose of the released in water, wherein the dissolved measured dose is at a pH of about 8.

17. The method of claim 16, wherein the dissolving the measured dose of the released granule or powder in water is in alkaline water.

18. The pharmaceutical composition of claim 1, wherein the one or more of additional excipients and adjuvants comprise sodium starch glycolate, crospovidone, croscarmellose sodium, glycerine, starches, hydrolyzed starches, partially pregelatinized starches, anhydrous lactose, lactose monohydrate, sugar alcohols, binders, carriers, lubricants, flow control agents, or crystallization retarders.

19. The pharmaceutical composition of claim 1, having a Euclidian distance of at least 260 or greater relative to a control composition, wherein the Euclidian distance is calculated with an e-tongue system for an aqueous suspension of 0.1-25 mg/ml of the composition at a pH ranging of about 8, wherein the composition and the control composition are the same other than the absence of the ion-pairing agent from the control composition.

* * * * *